(12) United States Patent
Samaranska et al.

(10) Patent No.: US 11,439,353 B2
(45) Date of Patent: Sep. 13, 2022

(54) MULTI-CANNULA SENSING DEVICE

(71) Applicant: Warsaw Orthopedic, Inc., Warsaw, IN (US)

(72) Inventors: Aneta Samaranska, Memphis, TN (US); Brian D. Koch, Memphis, TN (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 1242 days.

(21) Appl. No.: 15/180,971

(22) Filed: Jun. 13, 2016

(65) Prior Publication Data

US 2017/0354378 A1    Dec. 14, 2017

(51) Int. Cl.
*A61B 5/03*    (2006.01)
*A61B 5/00*    (2006.01)
(Continued)

(52) U.S. Cl.
CPC .............. *A61B 5/6848* (2013.01); *A61B 5/03* (2013.01); *A61B 5/036* (2013.01); *A61B 5/065* (2013.01);
(Continued)

(58) Field of Classification Search
CPC ...... A61M 25/01; A61M 19/00; A61M 25/06; A61M 25/065; A61M 5/427; A61M 2025/0037; A61M 25/0026; A61M 25/0028; A61M 25/0029; A61M 25/003; A61M 2025/0031; A61M 25/0032; A61M 2025/0034; A61M 2025/0036; A61M 2025/0039; A61M 2025/004; A61M 2025/0007; A61M 5/1582; A61M 25/0071; A61B 17/3401; A61B 17/3403; A61B 90/06; A61B 2090/064; A61B 2090/065; A61B 5/0048; A61B 5/0053; A61B 5/4896; A61B 5/4887; A61B 5/684; A61B 5/6843; A61B 5/6844; A61B 5/6846;
(Continued)

(56) References Cited

U.S. PATENT DOCUMENTS 4,808,157 A * 2/1989 Coombs ............. A61B 17/3401
                                                   604/158
5,517,846 A * 5/1996 Caggiani ................ A61B 5/031
                                                   600/486
(Continued)

FOREIGN PATENT DOCUMENTS

EP          2223662 A1     9/2010
WO       2014097301 A1     6/2014

*Primary Examiner* — Brandy S Lee
*Assistant Examiner* — Hong-Van N Trinh (57) ABSTRACT

The invention provides improved devices and apparatuses and related methods for sensing differences in pressure or other parameters in the environment of the body of a patient during passage of the device through one or more tissues. In one aspect, the devices and apparatuses of the invention are configured to sense differences in the environment of the body of the patient as the device passes through tissue adjacent to the epidural space to tissue of the epidural space. In one aspect, a dual cannula device comprising one or more sensors connected to a signaling component is provided for sensing passage into of the device into the epidural space and positioning therein. Methods of using same are also provided.

16 Claims, 8 Drawing Sheets

(51) Int. Cl.
  *A61B 5/06* (2006.01)
  *A61B 5/01* (2006.01)
  *A61B 5/145* (2006.01)

(52) U.S. Cl.
  CPC .......... *A61B 5/6847* (2013.01); *A61B 5/6851* (2013.01); *A61B 5/6852* (2013.01); *A61B 5/01* (2013.01); *A61B 5/14539* (2013.01)

(58) Field of Classification Search
  CPC ... A61B 5/6847; A61B 5/6848; A61B 5/6849; A61B 5/06; A61B 5/061; A61B 5/065; A61B 5/066; A61B 5/067; A61B 5/068; A61B 5/150748; A61B 6/12; A61B 8/0833; A61B 8/0841; A61B 8/085; A61B 5/03; A61B 5/031; A61B 5/032; A61B 5/033; A61B 5/035; A61B 5/036; A61B 5/037; A61B 5/038; A61B 5/6851; A61B 5/6852; A61B 5/01; A61B 5/015; A61B 5/14539; A61B 17/34; A61B 17/3415; A61N 1/0551
  See application file for complete search history.

(56) References Cited

U.S. PATENT DOCUMENTS

| | | | |
|---|---|---|---|
| 7,011,647 B2* | 3/2006 | Purdy | A61B 17/12113 604/164.04 |
| 9,597,480 B2* | 3/2017 | Purdy | A61B 5/0215 |
| 2003/0028147 A1* | 2/2003 | Aves | A61N 1/0551 604/164.06 |
| 2008/0146990 A1* | 6/2008 | Jenson | A61B 5/03 604/28 |
| 2008/0249467 A1* | 10/2008 | Burnett | A61B 1/313 604/117 |
| 2010/0256483 A1* | 10/2010 | Wall | A61B 1/3135 600/424 |
| 2011/0125107 A1 | 5/2011 | Slocum et al. | |
| 2013/0085413 A1 | 4/2013 | Tsamir | |

* cited by examiner

MULTI-CANNULA SENSING DEVICE

FIELD OF INVENTION

The present invention generally relates to the field of devices and apparatuses for obtaining access to and sensing differences in an environment of the body of a patient during passage of the device through one or more tissues of the body of the patient, such as tissues in and adjacent to the epidural space in the body of the patient, and more particularly to a multi-cannula device and stylet apparatus for sensing differences in the environment of the body of the patient during positioning of a portion of the device or apparatus in a low or negative pressure space (e.g., the epidural space), and methods of using same.

BACKGROUND

It is common to reduce or block pain associated with labor, disc herniation, and other acute or chronic events in a patient, by administering medication (anesthetics, analgesics, and the like) into the epidural space of the spinal canal of a patient. Contrast agents may similarly be administered into the epidural space for use in imaging. Current epidural methods typically use a Loss of Resistance (LOR) syringe to help physicians successfully locate the epidural space. In the LOR technique, air or saline is drawn into a syringe and pressure is applied to a plunger as the needle is advanced toward the epidural space. Upon entry into the epidural space, where a drop in pressure is experienced, the syringe contents are observably injected into the patient due to LOR, providing the medical practitioner with assurance that the syringe is properly located. Similar techniques may be used to detect entry into other low or negative pressure regions of the body, for example, the peritoneal cavity.

Despite wide use, LOR techniques and associated instruments remain subject to some difficulties. Excess air or saline delivered during administration of an epidural may be harmful to patients and/or may impede the onset and quality of epidural analgesia or anesthesia. Moreover, the LOR technique typically depends on direct visualization of displaced air or saline, and therefore may be inconsistent. It would be desirable to develop a sensing device for penetrating and sensing differences in the environment of the body of a patient as the device passes through one or more tissues of the body, such as differences that may be sensed during passage into and positioning in a low or negative pressure space of the body of the patient (e.g., epidural space) without the need to inject air or saline into the patient or to directly observe the release of air or saline into the patient. Furthermore, it would be desirable to provide a device for sensing differences in pressure and other parameters in the environment of the body of a patient during passage of such device through one or more tissues in the body of the patient.

The present invention satisfies these needs and provides other benefits and advantages in a novel and nonobvious manner.

SUMMARY OF THE INVENTION

The present invention relates generally to devices and apparatuses for obtaining access to and sensing entry into a low or negative pressure space, such as the epidural space of the spinal cord of a patient, and in particular, a multi-cannula device or stylet apparatus for sensing passage into the low or negative pressure space, and methods of using same. The present invention reduces or eliminates the need to inject air or saline into the patient and/or to directly observe the injection of air or saline into the patient as is common in typical LOR procedures.

In one embodiment of the invention, a dual cannula device for sensing differences in the environment of the body of a patient during passage of the device through one or more tissues in the body of the patient is provided. The dual cannula device comprises a first elongate member having a proximal end and distal end with a tip, and having an opening at each end. Disposed within the elongate member are first and second cannulas (i.e., hollow tubes), the first cannula having openings at the proximal end and the tip of the distal end, and the second cannula having openings at the proximal end and a portion of the distal end. A second member may be connected at a distal end thereof to the proximal end of the first elongate member and comprises a channel. The first cannula and channel define a lumen extending along a longitudinal axis of the device. The dual cannula device further comprises one or more sensors; and one or more signaling components connected to the one or more sensors for relaying data from the one or more sensors to a user when the first elongate member passes through one or more tissues. The first elongate member may comprise a needle or stylet, and the second member may comprise a needle hub or a stylet hub. In an alternative embodiment, the first elongate member may be a single cannula needle with an outer sleeve comprising a second cannula.

In one aspect, the dual cannula device may be useful for sensing passage into a low or negative pressure space of the body of a patient (e.g., the epidural space in the spinal canal of the patient). The one or more sensors are configured to relay data from the one or more sensors to a user when the first elongate member is positioned within the low or negative pressure space of the patient.

In one embodiment of the invention, a stylet apparatus for sensing entry into a low or negative pressure space of the body of a patient is provided. The stylet apparatus generally comprises a hollow stylet having proximal and distal ends and a stylet hub having proximal and distal ends. The proximal end of the hollow stylet is connected to the distal end of the stylet hub. The stylet apparatus further comprises one or more sensors disposed within the distal end of the hollow stylet and a signaling component connected to the one or more sensors for relaying data from the one or more sensors to a user when the stylet is positioned in the low or negative pressure space.

In another embodiment of the invention, a method of using the aforementioned dual cannula device is provided. The method generally comprises the steps of providing the aforementioned dual cannula device or, penetrating skin of the patient in a region of a low or negative pressure space, such as with the distal tip of the device, advancing the device through the access path into tissue of the patient until the signaling component signals entry into the low or negative pressure space, and administering treatment media to the low or negative pressure space through the lumen of the device. Other methods of using the device for sensing changes in the environment of the body of a patient during passage of the device through one or more tissues in the body of the patient also fall within the scope of the invention.

In one embodiment of the invention, a method of using the aforementioned sensing stylet apparatus is provided. The method comprises the same or similar steps discussed above, and may further comprise the steps of introducing the sensing stylet apparatus into the lumen of a needle prior to passing the needle through one or more tissues and removing the stylet from the lumen of the needle prior to administering treatment media to the patient.

The foregoing summary of invention and the following description, claims, and drawings disclose exemplary embodiments, and do not limit the scope of the present invention. Additional embodiments of the present invention will be apparent from consideration of the detailed description, drawings, and claims of this disclosure. Moreover, it will be understood that the present invention may be employed with other components and instruments (e.g., catheters, needles, stylets, hubs, wires, lines) known in the field.

DETAILED DESCRIPTION

The exemplary embodiments of the invention and related methods of use disclosed are discussed generally in terms of medical devices for penetration of tissue and delivery of medications, such as a drug, to a recipient, such as a medical patient, particularly devices for sensing changes or differences in the environment of the body of a patient during passage of the device through one or more tissues in the body of the patient. More particularly, the exemplary embodiments of the invention and related methods of use disclosed are discussed in terms of medical devices for penetrating and sensing passage of the invention into a low or negative pressure space (e.g., epidural space adjacent the spinal cord) of the body of a patient and positioning therein, and methods of using the same to treat a patient, such as by delivering medications for epidural analgesia or anesthesia or imaging agents. The devices and methods of the present invention will generally reduce or eliminate the need to inject air or saline into the patient or to directly observe such an injection to detect entry into the low or negative pressure space.

It is envisioned that the present disclosure may be employed to treat a patient by reducing or blocking pain associated with medical conditions and procedures (e.g., labor, disc herniation, imaging) by administering medication (e.g., anesthetics, analgesics, drugs) into the epidural space of a patient by providing a device for sensing entry and passage into the epidural space of a patient which avoids the typical air or saline injections common in the LOR technique. The dual cannula device of the invention may be employed to sense passage into and positioning in the epidural space of the patient by sensing differences in measurable parameters in the environment of the body of the patient, for example, pressure, temperature, viscosity, pH, chemistry, electrical charge or signal, force, energy, wavelength, frequency, displacement, orientation, or a combination thereof, between one or more tissues, as the device passes into and/or is positioned in the epidural space. Such parameters sensed by one or more sensors of the dual cannula device will generally be signaled to the user by a signal relaying component of the device.

While the present disclosure generally discloses embodiments of the invention in terms of epidural treatments of a patient, it is contemplated that the present disclosure may be employed with other related applications that require precise passage and positioning of the device through one or more tissues, for example, passage into a low or negative pressure space located in an internal region of a patient (e.g., chest, brain, peritoneal cavities), including those associated with diagnostics and therapeutics. Further it is contemplated that other applications which would benefit from detection of differences in the environment of the device during passage through one or more tissues of the patient wherein the one or more tissues possess measurably different characteristics, such as in the aforementioned parameters. Further, embodiments of the invention may be employed in a variety of medical procedures, including, for example, in cannulation and catheterization, tube placement, punctures, and laparoscopy, and with a variety of injection media, for example, medications, drugs, imaging agents, and anesthesia.

It is further contemplated that the disclosed multi-cannula sensing device and related apparatuses and methods of use may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The invention of the present disclosure may also be used on animals, bone models and other non-living substrates, such as, for example, in training, testing and demonstration.

The present embodiments may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, upward, downward, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition, Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue (e.g., ligaments, tendons, fascia, skin, fibrous tissues, fat, synovial membranes, muscles, nerves and blood vessels), blood, marrow, cartilage and/or bone unless specifically referred to otherwise.

The components of the invention can be fabricated from biologically acceptable materials suitable for medical applications, including metals, synthetic polymers, ceramics and bone material and/or their composites, depending on the particular application and/or preference of a medical practitioner. For example, the one or more components of the invention, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the invention may have material composites, including the above materials, to achieve various desired characteristics such as strength, rigidity, elasticity, compliance, biomechanical performance, durability and radiolucency or imaging preference. The components of the invention, individually or collectively, may also be fabricated from a heterogeneous material such as a combination of two or more of the above-described materials. The components of the invention may be monolithically formed, integrally connected or include fastening elements and/or instruments, as described herein.

For the purposes of promoting an understanding of the principles of the invention, reference will now be made to exemplary embodiments of the present disclosure, which are illustrated in the accompanying figures (FIGS. 1-8), and specific language will be used to describe the same. Alternate embodiments are also disclosed. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

According to the present invention, a dual cannula device 100 for sensing changes in the environment of the body of a patient during passage of the device through one or more tissues in the body of the patient is provided. Tissues of the body are diverse in nature, and may vary at least in terms of density, function, chemical and structural makeup, location in the body, and the like. Device 100 is configured to sense changes in the environment of the device upon passage from one tissue to another. For example, device 100 may sense differences between one or more tissues, for example, pressure, temperature, viscosity, pH, chemistry (e.g., biomarkers, enzymes, oxygenation level), electrical charge or signal, force (e.g., tissue resistance or impedance), energy, frequency, or wavelength (e.g., light, color), displacement (e.g., GPS), or orientation (e.g., tilt, rotation), or a combination thereof, that may be sensed and measured as a portion of the device passes from one tissue type to another, thereby permitting the user to identify when the device is positioned in a desired target region of the body. The user may correlate data provided by the device with known environmental parameters of any given tissue type.

Device 100 generally comprises a first elongate member 10 having a proximal end 11 and distal end 12 and is open at each end. Device 100 may have one or more cannulas disposed therein. Device 100 may be a dual cannula device having a first cannula 14 and a second cannula 15 disposed therein. First cannula 14 comprises an opening 14a at proximal end 11 and an opening 14b at a tip 13 of distal end 12. Typically, second cannula 15 comprises an opening 15a at proximal end 11 and an opening 15b at a portion of distal end 12, however, it will be understood that opening 15b may be positioned at other locations within second cannula 15. Dual cannula device 100 also comprises a second member 20 connected at a distal end 22 thereof to the proximal end 11 of first elongate member 10 and comprising a channel 23, first cannula 14 and channel 23 together define a lumen extending along a longitudinal axis L of the device. Dual cannula device 100 further comprises one or more sensors 16, and one or more signaling components 40 connected to one or more sensors 16 for relaying data from said one or more sensors to a user when the first elongate member passes through one or more tissues (e.g., through subcutaneous fascia 30 into epidural space 31).

Figure 1:
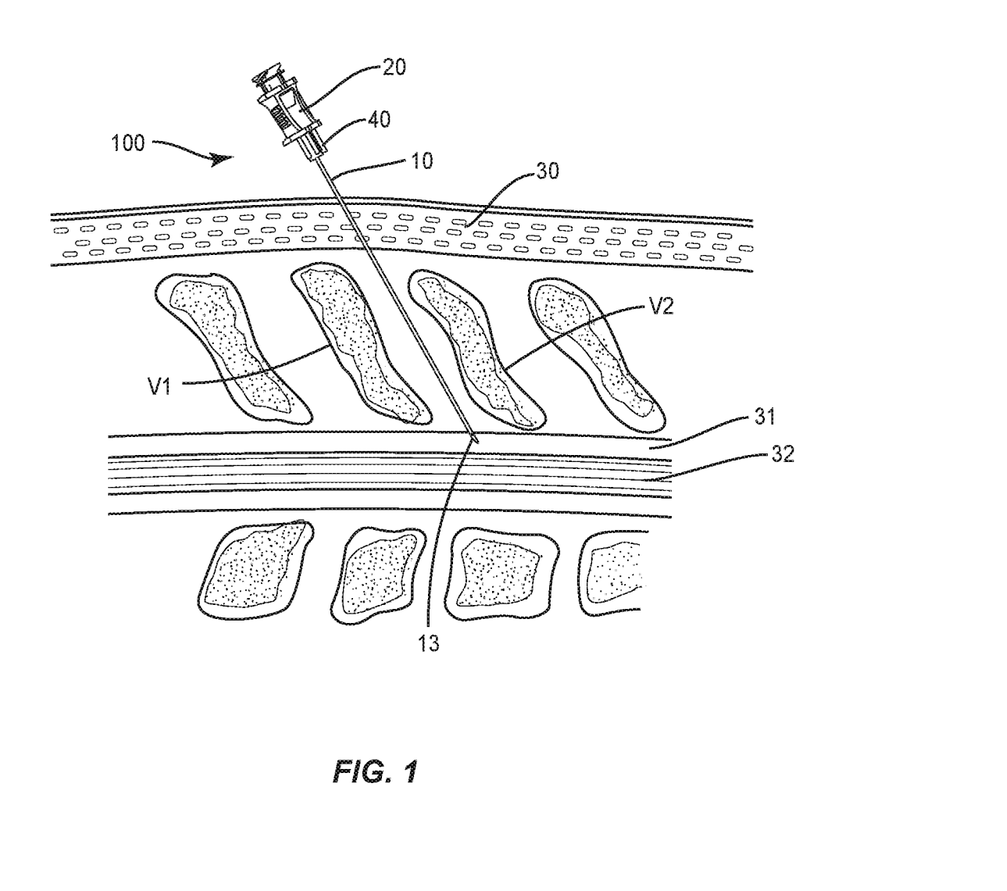
FIG. 1 is a perspective view of an embodiment of the dual cannula device in a cross-section of the epidural space of a patient.

Referring now to FIG. 1, shown therein is a perspective view of a partial cross-section of multi-cannula sensing device 100 positioned in an epidural space 31 adjacent the spinal cord in the body of a patient in accordance with the invention. Device 100 will be particularly useful for sensing and providing a signal to the user when the device is suitably positioned for administration of treatment media (e.g., analgesia, anesthesia, drugs, medication, or imaging media) into epidural space 31. A portion of multi-cannula device 100 penetrates a first tissue, for example, subcutaneous fascia 30, between adjacent vertebra V1 and V2 at a depth at which distal tip 13 of a first elongate member 10 resides in a second tissue, epidural space 31, but does touch or penetrate a third tissue, the dura of spinal cord 32. Multi-cannula device 100 is configured, as described herein, to provide a signal (e.g., visual, audio) to the user when one or more sensors 16 of the device sense environmental changes upon passage through one or more tissues, such as passage through surrounding tissue of the epidural space to tissue of epidural space 31. As device 100 senses differences in the environment related to passage between one or more tissues of the body, device 100 may be configured to alert the user when distal tip 13 may penetrate or pass through an undesirable location of the body, such as near or at the dura mater of the spinal cord 32 of the patient.

Figure 2:
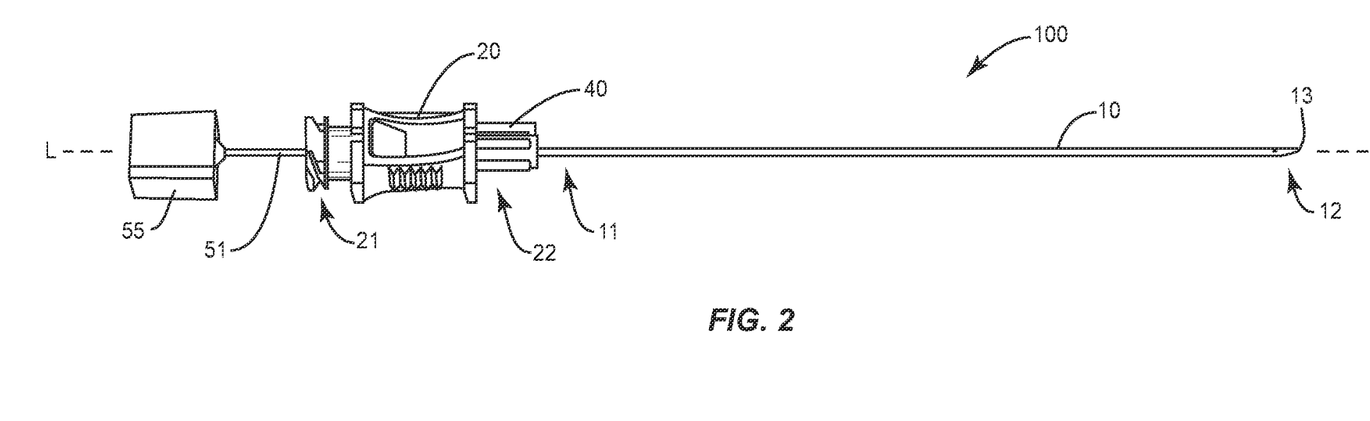
FIG. 2 is a side perspective view of an embodiment of he dual cannula device having a stylet inserted therein.
Figure 2A:
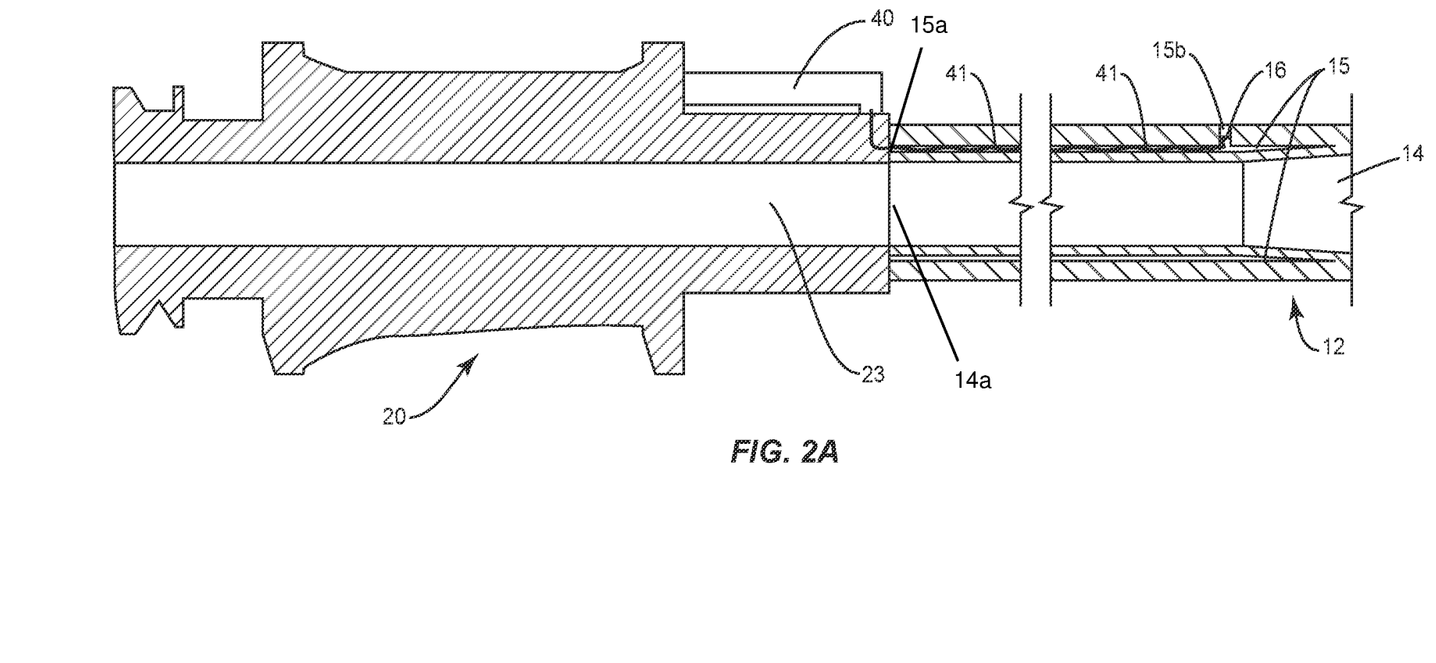
FIG. 2A is a cross-sectional view of FIG. 2.

Multi-cannula sensing device 100 generally comprises a first elongate member 10 having a proximal end 11 and a distal end 12 as in FIG. 2. Distal end 12 comprises a tip 13. Typically, first elongate member 10 is a needle, but it may also be a stylet. The needle may be or be similar to, for example, a Tuohy, Weiss, Hustead, or Crawford style epidural needle. However, it will be understood that the needle, and particularly tip 13, may be of any shape known in the field suitable to permit a user to penetrate the skin of a patient and penetrate through tissue in order to access epidural space 31, for example, a blunt, beveled, tapered, angled, sharpened, flat, straight or curved configuration, or some combination thereof.

In a typical embodiment, disposed within first elongate member 10 are a first cannula 14 and a second cannula 15 (i.e., first and second hollow tubes). However, it will be understood that additional cannulas may be provided in accordance with the particular application. The hollow space of first cannula 14 may be larger or substantially larger than the hollow space of second cannula 15. For example, first cannula 14 may have an inner diameter D larger than an inner diameter D2 of second cannula 15 as in FIG. 3B. Generally first cannula 14 and second cannula 15 are not removable from first elongate member 10. In one embodiment, first cannula 14 and second cannula 15 will be welded components of first elongate member 10. However, it will also be understood that alternative embodiments of the invention are contemplated in which first cannula 14 is disposed within first elongate member 10, and second cannula 15 is disposed within an outer sleeve 19 surrounding a circumference of first elongate member 10, as in FIGS. 5-5B.

First cannula 14 defines a first lumen and typically extends along the entire length of first elongate member 10 along longitudinal axis L and comprises opening 14a at proximal end 11 and opening 14b at distal end 12, more typically at tip 13. Openings 14a and 14b may have various cross-sections, for example, cylindrical or elliptical. First cannula 14 is generally configured to accommodate instruments for inserting into the lumen of a needle such as a catheter, stylet, wire.

Second cannula 15 defines a second lumen and may extend along the entire length, more typically a portion of, elongate member 10 along longitudinal axis L. The first elongate 10 having a wall 24 separating the first and second lumens. Second cannula 15 comprises opening 15a at proximal end 11 and opening 15b at or near distal end 12. Opening 15a may have various cross-sections, for example, cylindrical or elliptical. Opening 15b may also have various cross-sections, for example, square, rectangular, cylindrical or elliptical, and may further be any size suitable to permit one or more sensors 16 to sense entry into epidural space 31. It will be understood that opening 15b may be positioned at any location along the length of second cannula 15, for example, at or near proximal end 11 or distal end 12 or along any portion of inner surface 17 or outer surface 18 of second cannula 15. In some embodiments, second cannula 15 extends from proximal end 11 and terminates at or near opening 15b as in FIGS. 3A, 4A, and 5A. The hollow space provided by second cannula 15 and the second lumen will be suitably sized to accommodate one or more sensors 16 (e.g., membranes) and wires 41 as discussed herein.

Figure 3:
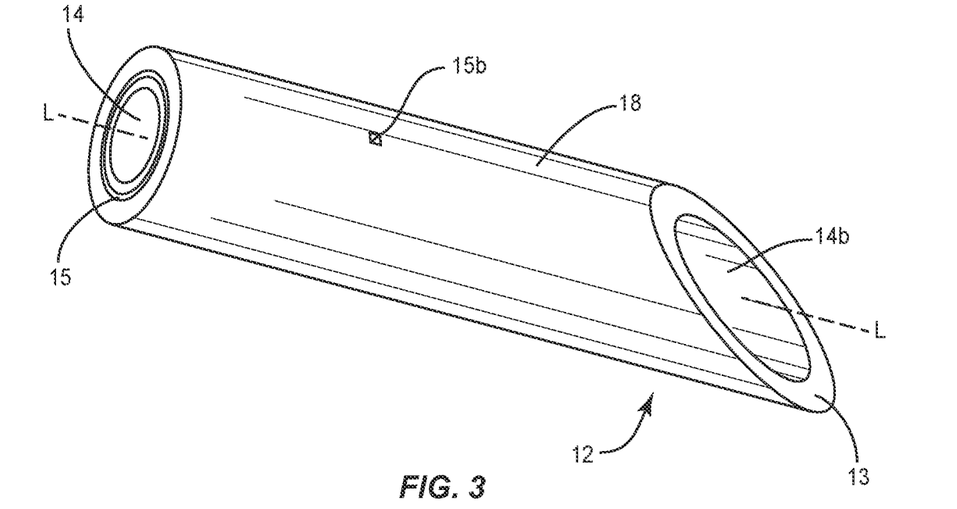
FIG. 3 is an enlarged perspective view of a distal end of an embodiment of a first elongate member of the dual cannula device wherein a first cannula is disposed within a second cannula.
Figure 3A:
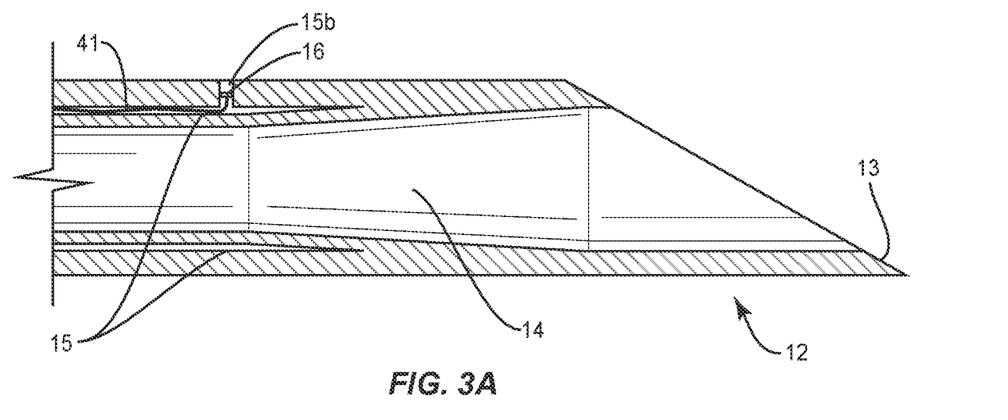
FIG. 3A is a cross-sectional view of FIG. 3.
Figure 3B:
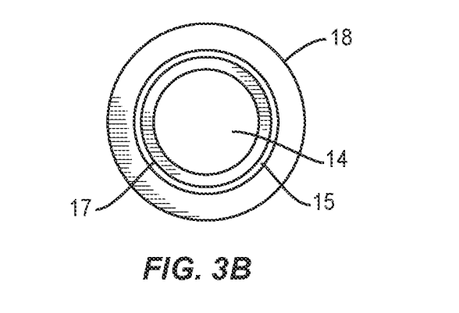
FIG. 3B is a cross-section of FIG. 3 as viewed from the proximal end of the first elongate member.
Figure 4:
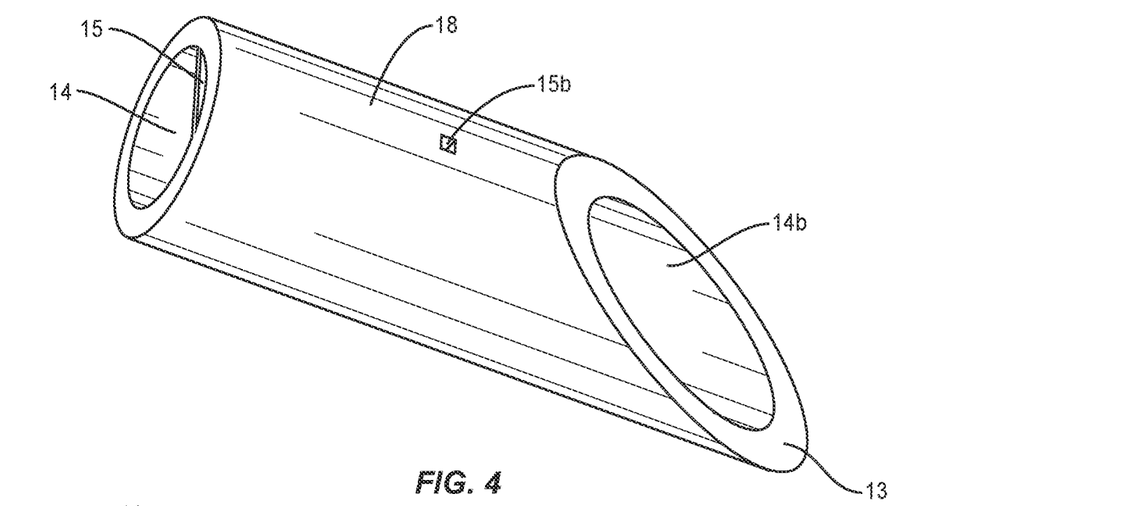
FIG. 4 is an enlarged perspective view of a distal end of an embodiment of the first elongate member of the dual cannula device wherein a first cannula and a second cannula are disposed side-by-side with the first-elongate member.
Figure 4A:
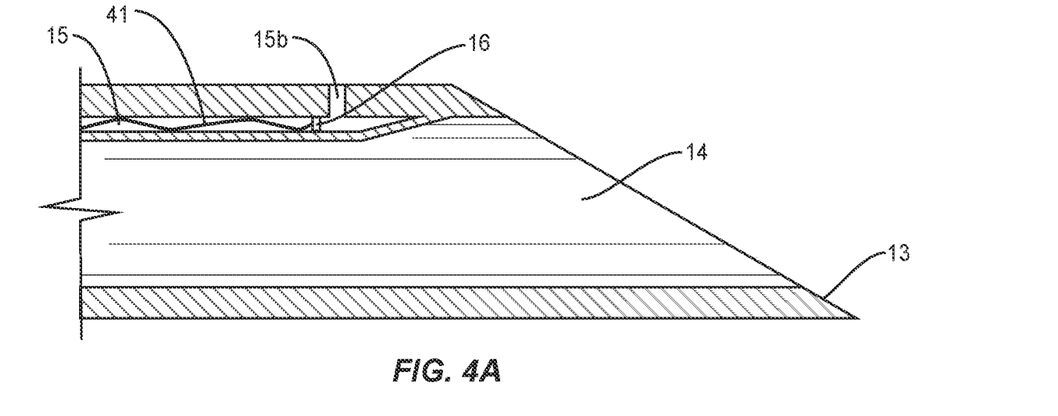
FIG. 4A is a cross-sectional view of FIG. 4.
Figure 4B:
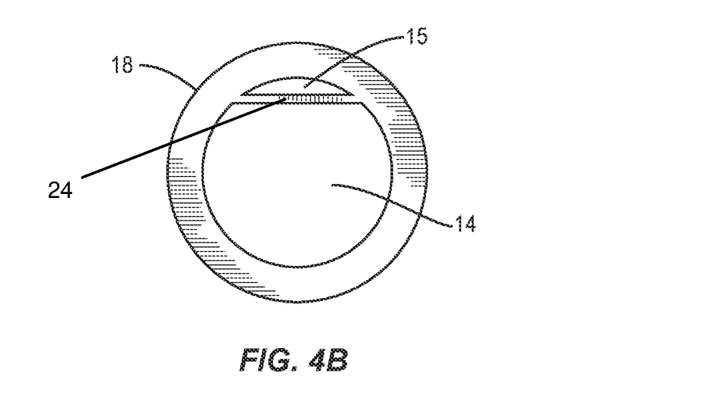
FIG. 4B is a cross-section of FIG. 4 as viewed from the proximal end of the first elongate member.
Figure 5:
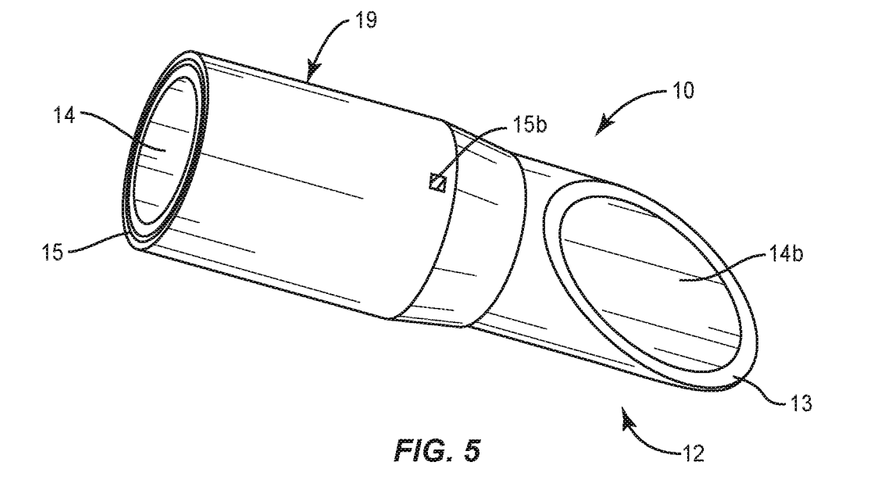
FIG. 5 is an enlarged perspective view of a distal end of an alternative embodiment of the dual cannula device wherein a second cannula is disposed in an outer sleeve surrounding a single cannula of a first elongate member.
Figure 5A:
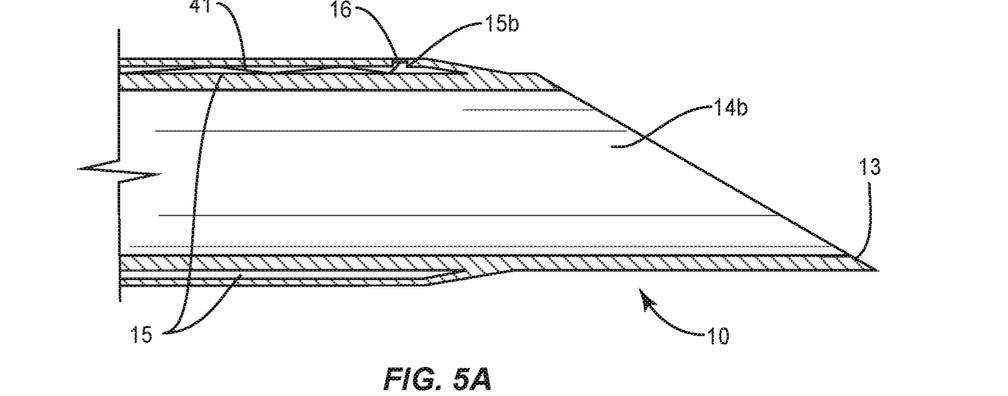
FIG. 5A is a cross-sectional view of FIG. 5.
Figure 5B:
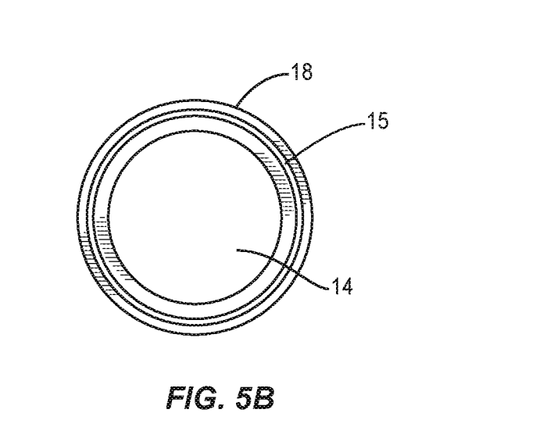
FIG. 5B is a cross-section of FIG. 5 as viewed from the proximal end of the first elongate member.

First cannula 14 and second cannula 15 may be disposed in several configurations relative to each other. In one embodiment, first cannula 14 is disposed within and surrounded by second cannula 15 itself disposed within first elongate member 10 (FIGS. 3-3B). In an alternative embodiment, first cannula 14 and second cannula 15 may be side-by-side within first elongate member 10 (FIGS. 4-4B), though they may vary in inner diameter. In another alternative embodiment, first cannula 14 is disposed within first elongate member 10, while second cannula 15 may be located in an outer sleeve 19 engaging a circumference of first elongate member 10 (FIG. 5-5B).

The present invention further comprises a second member 20 having a proximal end 21 and a distal end 22, Second member 20 comprises a hollow channel 23 extending along longitudinal axis L such that first cannula 14 and hollow channel 23 may be aligned to together define a lumen for inserting instruments useful in administering treatment media to a low or negative pressure region of a patient, such as a catheter, stylet, wire. Second member 20 may be a needle hub or stylet hub.

Device 100 further comprises one or more sensors 16 disposed within second cannula 15. Typically the one or more sensors will be located at or near opening 15b, however, it will be understood that the one or more sensors 16 may be positioned at any site within second cannula 15. In an alternative embodiment, the one or more sensors may be disposed within second member 20. Sensors 16 may be membranes, wires, or the like configured to sense and measure various parameters detectable upon or subsequent to entry of distal tip 13 into epidural space 31, including but not limited to, differences in pressure, temperature, viscosity, pH, chemistry, electrical charge or signal, force, energy, wavelength, frequency, displacement, orientation, or a combination thereof, between one or more tissues adjacent to the epidural space and tissues of the epidural space. In one embodiment, at least one sensor is configured to sense and measure pressure upon entry into epidural space 31.

In some embodiments, the device 100 comprises two or more sensors 16 configured to sense and measure at least one of the aforementioned parameters and located in different components of device 100. In one embodiment, at least one sensor will be disposed within second member 20, and an additional one or more sensors 16 will be disposed within second cannula 15. The differently positioned sensors may both detect and measure pressure, or alternatively, may detect and measure distinct sensory changes upon entry into epidural space 31.

In a further embodiment of the invention, one or more sensors 16 may be further adapted to measure or sense penetration of distal tip 13 into the dura mater of the spinal cord such that device 100 may be usefully employed to alert the user when such event has occurred by communicating data from one or more sensors 16 to a signaling component 40 connected thereto.

Device 100 further comprises a signaling component 40 disposed within and/or on second member 20 and connected to the aforementioned one or more sensors 16. Signaling component 40 relays a signal to the user when one or more sensors 16 detect a change in the environment of distal tip 13 which indicates entry into epidural space 31. Signaling component 40 may comprise various configurations for providing a signal to the user, including but not limited to, a visual display (e.g., LED, or audio component. In one embodiment, signaling component 40 may be connected by one or more wires 41 disposed within second cannula 15 to the one or more sensors 16. In another embodiment, signaling component 40 will be wirelessly connected to one or more sensors 16. In one embodiment, signaling component 40 is enclosed within second member 20. Signaling component 40 will be particularly useful for indicating entry of the device into the epidural space without the need to inject saline or air into the patient or to observe the same. In one embodiment, signaling component 40 will comprise a signal (e.g., LED signal) 42 connected to a microcontroller 43 and a battery 44, as in FIG. 7. In some embodiments, signaling component 40 may be located remotely (e.g., computer, mobile device) rather than embedded in or on device 100.

It is envisioned that device 100 may be employed with other instruments for treating a patient by delivering treatment media to a low or negative pressure region of the body of the patient, including but not limited to, a catheter, stylet, or wire.

Figure 6:
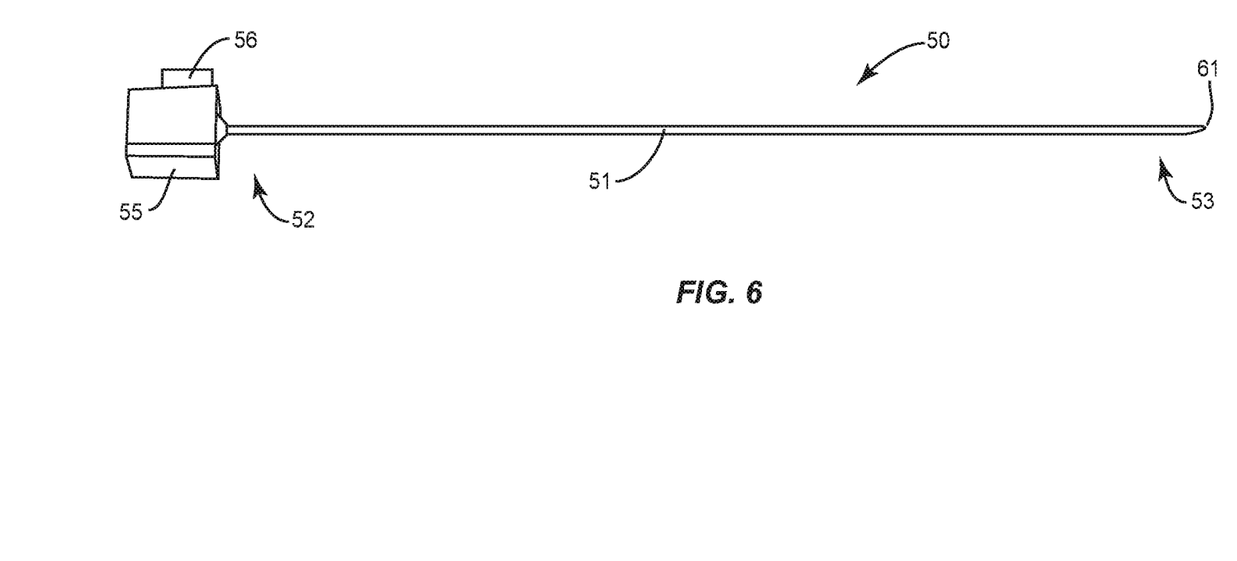
FIG. 6 is a perspective view of an embodiment of the sensing stylet apparatus.
Figure 7:
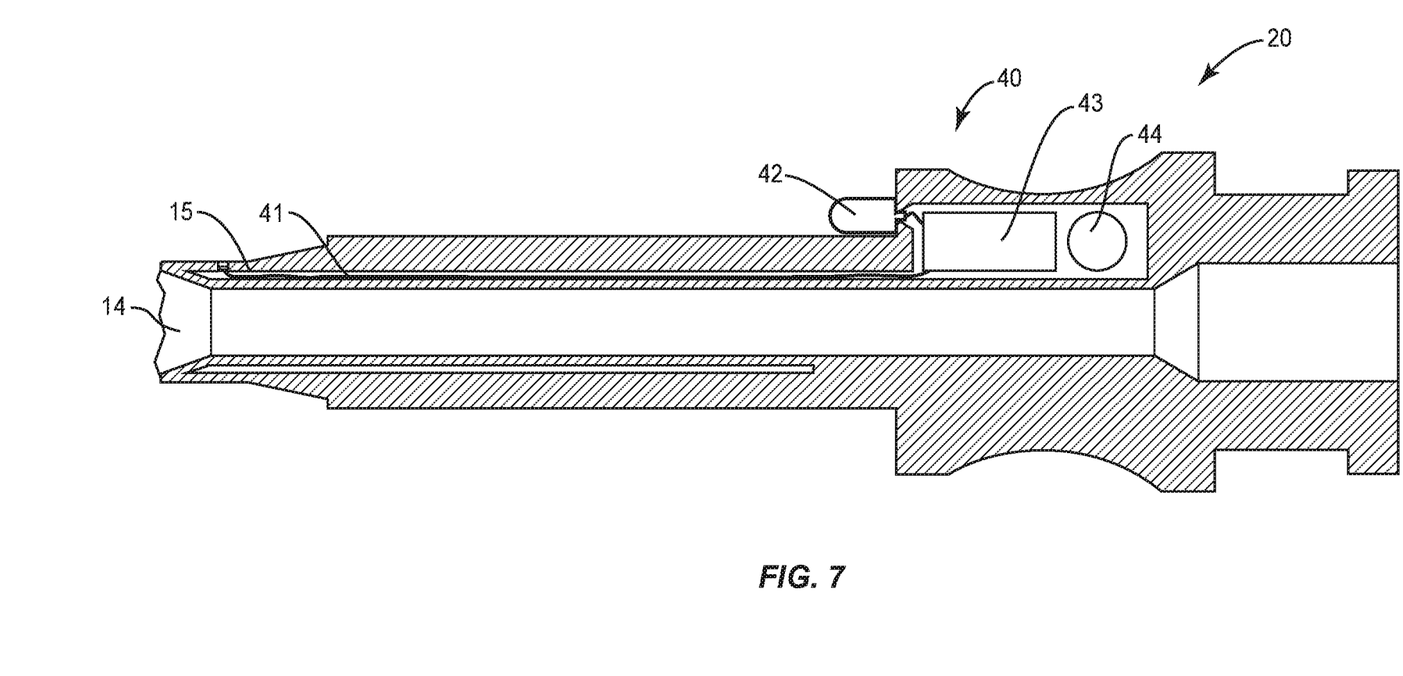
FIG. 7 is an enlarged cross-sectional view of an embodiment of the signaling component of the dual cannula device.
Figure 8:
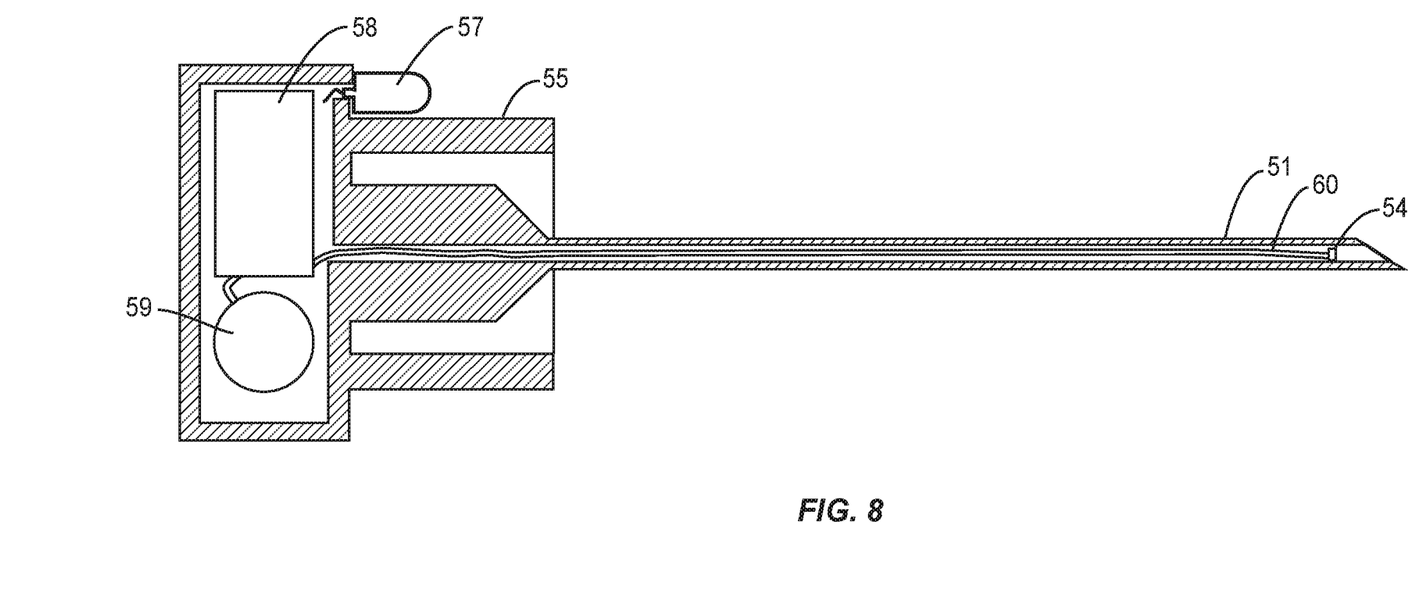
FIG. 8 is an enlarged cross-sectional view of an embodiment of the signaling component of the sensing stylet apparatus.

Referring to FIG. 6, another embodiment of the present invention is a sensing stylet apparatus 50 for sensing entry into epidural space 31. Stylet apparatus 50 generally comprises a hollow stylet 51 connected to a stylet hub 55 and having a proximal end 52 and a distal end 53. One or more sensors 54 may be disposed within hollow stylet 51 or stylet hub 55. A signaling component 56 connected to one or more sensors 54 may be disposed fully or partially within or on stylet hub 55. In one embodiment, signaling component 56 will comprise a signal (e.g., LED signal) 57 connected to a microcontroller 58 and a battery 59, as in FIG. 8. In an alternative embodiment, signaling component 56 may be located remotely (e.g., computer, mobile device) rather than embedded in or on apparatus 50.

Hollow stylet 51 generally comprises a minimal inner diameter sized to avoid coring, puncturing, or rupturing tissue or bone of the patient during the procedures, including during passage of the apparatus 50 through the body. Hollow stylet 51 has a distal tip 61 which may be configured similarly to tip 13 of device 100. Hollow stylet 51 further comprises an opening 62 at distal end 53 of apparatus 50. One or more sensors 54 and signaling component 56 may be configured and connected in any manner as described for one or more sensors 16 and signaling component 40 of dual cannula device 100. In one embodiment, one or more sensors 54 are disposed within hollow stylet 51. In one embodiment, one or more sensors 54 sense differences in pressure, temperature, viscosity, pH, chemistry, electrical charge or signal, force, energy, wavelength, frequency, displacement, orientation, or a combination thereof, between one or more tissues, during passage into and positioning in epidural space 31. In one embodiment, stylet apparatus 50 will comprise two or more sensors which may sense different parameters upon entry into the epidural space and/or may be positioned in distinct locations of the apparatus. In one embodiment, one or more sensors 54 are connected to signaling component 56 by one or more wires 63. In another embodiment, the connection between one or more sensors 54 and signaling component 56 will be wireless. In one embodiment, stylet apparatus 50 will be usefully employed by insertion into the lumen of a needle configured to penetrate a low or negative pressure space in the body of a patient, such as the epidural space.

Further in accordance with the present invention, a method of treating a patient is provided. The method generally comprises the steps of providing the aforementioned device 100, penetrating skin of the patient in a region of the spine with the distal end of the device to provide an access path through one or more tissues, advancing the distal end of the device through the access path, and sensing changes in the environment during passage from a first tissue to one or more additional tissues with the device. In some embodiments, the second tissue will be the epidural space of the patient. In some embodiments, the method further comprises administering treatment media into the epidural space through the device. The method may further comprise inserting a stylet into the lumen of the device prior to advancing the distal end of the device towards the epidural space of the patient, and removing the stylet following entry of the device into the epidural space. The method may further comprise administering epidural medication or similar media through an instrument inserted into the lumen of the device, for example, a catheter. In some embodiments, the device senses changes in pressure of the environment of the device during passage of the device through one or more tissues of the patient.

Another method of the invention comprises the steps of puncturing skin of the patient in a region of the spine, inserting the aforementioned stylet apparatus 100 into a lumen of the needle, advancing the needle and stylet apparatus into one or more tissues of the patient, and sensing passage into the epidural space with the stylet apparatus. The method may further comprise removing the stylet from the lumen of the needle and administering treatment media into the epidural space through the needle following removal of the stylet.

While the exemplary instruments and methods disclosed herein are described in terms of the epidural space, it will be understood that other applications relating to low or negative pressure regions in the body of a patient fall within the scope of the invention. It will further be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

The invention claimed is:

1. A dual cannula device for sensing difference in an environment of a body of a patient during passage of the dual cannula device through one or more tissues in the body of the patient comprising:
   an elongate first member having a proximal end, an opposite distal end, a length extending between the proximal end and the distal end of the elongate first member, the elongate first member having disposed therein a first cannula having a first lumen and a second cannula having a second lumen, wherein the first and second cannulas are in a side-by-side configuration, the first cannula having a distal end that extends distally from a distal end of the second cannula, the first lumen extending through and along the length of the elongate first member between a first opening at a proximal end of the first cannula and a second opening at the distal end of the first cannula, the second lumen extending through and along a portion of the length of the elongate first member between a third opening at a proximal end of the second cannula and a fourth opening adjacent the distal end of the second cannula, the elongate first member having a wall separating the first and second cannulas, wherein, in a cross-section perpendicular to the length of the elongate first member, a first surface of the wall and a first interior arcuate portion of the first cannula forms a first cross-sectional area of the first lumen, and a second surface of the wall and a second interior arcuate portion of the second cannula forms a second cross-sectional area of the second lumen, the first interior arcuate portion having a shape corresponding to a majority of a circle such that the first cross-sectional area is substantially larger than the second cross sectional area;
   a second member having a proximal end, an opposite distal end, a length extending between the proximal end of the second member and the distal end of the second member, the second member connected at the distal end of the second member to the proximal end of the alongate first member, the second member including a channel extending between the proximal end of the second member and the distal end of the second member, the channel communicating with the first lumen;
   one or more sensors positioned in the second lumen; and
   a signaling component including a light source, the signaling component being connected to the one or more sensors and being configured to illuminate the light source when the one or more sensors sense that the elongate first member passes through the one or more tissues, the light source being provided on the second member.

2. The dual cannula device of claim 1, wherein the one or more sensors are configured to sense differences in pressure, temperature, viscosity, pH, chemistry, electrical charge or signal, force, energy, wavelength, frequency, displacement, orientation, or a combination thereof, between the one or more tissues.

3. The dual cannula device of claim 1, wherein the dual cannula device senses differences in pressure when the elongate first member passes through the one or more tissues of or adjacent to an epidural space of the patient.

4. The dual cannula device of claim 1 wherein the elongate first member is a needle and the second member is a needle hub.

5. The dual cannula device of claim 1, wherein the one or more sensors are located adjacent the distal end of the elongate first member.

6. The dual cannula device of claim 1, wherein the one or more sensors are connected to the signaling component wirelessly or via one or more wires.

7. The dual cannula device of claim 1, wherein the elongate first member includes an exterior surface, and the fourth opening is formed through the exterior surface.

8. The dual cannula device of claim 7, wherein the elongate first member includes a longitudinal axis extending through the proximal end and the distal end of the elongate first member, wherein the second lumen includes a primary portion extending in a direction substantially aligned with the longitudinal axis, and a brance portion adjacent the distal end of the elongate first member that extends in a direction transverse to the longitudinal axis.

9. A dual cannula device for sensing differences in an environment of a body of a patient during passage of the dual cannula device through one or more tissues in the body of the patient comprising:
   an elongate first member having a proximal end, an opposite distal end, a length extending between the proximal end and the distal end of the elongate first member, a longitudinal axis extending through the proximal end and the distal end, the elongate first member having disposed therein a first cannula having a first lumen and a second cannula having a second lumen, wherein the first and second cannulas are in a side-by-side configuration, the first cannula having a distal end that extends distally from a distal end of the second cannula, the first lumen substantially aligned with the longitudinal axis and extending through and along the length of the elongate first member between a first opening at a proximal end of the first cannula and a second opening at the distal end of the first cannula, portions of the second lumen substantially aligned with the longitudinal axis and extending through and along a portion of the length of the elongate first member between a third opening at a proximal end of the second cannula and a fourth opening adjacent the distal end of the second cannula, the elongate first member having a wall separating the first and second cannulas, wherein, in a cross-section perpendicular to the longitudinal axis, a first surface of the wall and a first interior arcuate portion of the first cannula forms a first cross-sectional area of the first lumen, and a second surface of the wall and a second interior arcuate portion of the second cannula forms a second cross-sectional area of the second lumen, the first interior arcuate portion having a shape corresponding to a majority of a circle such that the first cross-sectional area is substantially larger than the second cross sectional area;
   one or more sensors positioned in the second lumen; and
   a signaling component including a light source, the signaling component being connected to the one or more sensors and being configured to illuminate the light source when the one or more sensors sense that the elongate first member passes through the one or more tissues.

10. The dual cannula device of claim 9, wherein the one or more sensors are configured to sense differences in pressure, temperature, viscosity, pH, chemistry, electrical charge or signal, force, energy, wavelength, frequency, displacement, orientation, or a combination thereof, between the one or more tissues.

11. The dual cannula device of claim 9, wherein the elongate first member includes an exterior surface, and the fourth opening is formed through the exterior surface.

12. The dual cannula device of claim 11, wherein the second lumen includes a primary portion extending in a direction substantially aligned with the longitudinal axis, and a branch portion adjacent the distal end of the elongate first member that extends in a direction transverse to the longitudinal axis.

13. A dual cannula device for sensing differences in an environment of a body of a patient during passage of the dual cannula device through one or more tissues in the body of the patient comprising:

an elongate first member having a proximal end, an opposite distal end, a length extending between the proximal end and the distal end of the elongate first member, a longitudinal axis extending through the proximal end and the distal end, the elongate first member having disposed therein a first cannula having a first lumen and a second cannula having a second lumen, wherein the first and second cannulas are in a side-by-side configuration, the first cannula having a distal end that extends distally from a distal end of the second cannula, the first lumen substantially aligned with the longitudinal axis and extending through and along the length of the elongate first member between a first opening at a proximal end of the first cannula and a second opening at the distal end of the first cannula, portions of the second lumen substantially aligned with the longitudinal axis and extending through and along a portion of the length of the elongate first member between a third opening at a proximal end of the second cannula and a fourth opening adjacent distal end of the second cannula, the elongate first member having a wall separating the first and second cannulas, wherein, in a cross-section perpendicular to the longitudinal axis, a first surface of the wall and a first interior arcuate portion of the first cannula forms a first cross-sectional area of the first lumen, and a second surface of the wall and a second interior arcuate portion of the second cannula forms a second cross-sectional area of the second lumen, the first interior arcuate portion having a shape corresponding to a majority of a circle such that the first cross-sectional area is substantially larger than the second cross sectional area;

one or more sensors positioned in the second lumen;

a second member connected at a distal end thereof to the proximal end of the elongate first member, the second member including a channel communicating with the first lumen; and a signaling component including a light source, the signaling component connected to the one or more sensors and being configured to illuminate the light source when the one or more sensors sense that the elongate first member passes through the one or more tissues, the light source being provided on the second member.

14. The dual cannula device of claim 13, wherein the one or more sensors are configured to sense differences in pressure, temperature, viscosity, pH, chemistry, electrical charge or signal, force, energy, wavelength, frequency, displacement, orientation, or a combination thereof, between the one or more tissues.

15. The dual cannula device of claim 13, wherein the elongate first member includes an exterior surface, and the fourth opening is formed through the exterior surface.

16. The dual cannula device of claim 15, wherein the second lumen includes a primary portion extending in a direction substantially aligned with the longitudinal axis, and a branch portion adjacent the distal end of the elongate first member that extends in a direction transverse to the longitudinal axis.

* * * * *